(12) United States Patent
Cardoso

(10) Patent No.: US 7,156,097 B2
(45) Date of Patent: *Jan. 2, 2007

(54) NASAL CANNULA

(76) Inventor: Norman Cardoso, 111 Ross Rd., Satsuma, FL (US) 32189

( * ) Notice: Subject to any disclaimer, the term of this patent is extended or adjusted under 35 U.S.C. 154(b) by 343 days.

This patent is subject to a terminal disclaimer.

(21) Appl. No.: 10/659,008

(22) Filed: Sep. 10, 2003

(65) Prior Publication Data

US 2004/0045553 A1   Mar. 11, 2004

Related U.S. Application Data

(63) Continuation-in-part of application No. 09/994,571, filed on Nov. 27, 2001, now Pat. No. 6,669,712.

(60) Provisional application No. 60/409,771, filed on Sep. 10, 2002.

(51) Int. Cl.
*A61M 16/00* (2006.01)
*A61M 15/08* (2006.01)
*A61M 31/00* (2006.01)

(52) U.S. Cl. .................. 128/206.11; 128/207.18; 604/94.01

(58) Field of Classification Search ........... 128/207.18, 128/207.17, 207.13, 207.11, 206.28, 206.27, 128/206.14, 206.11, 204.18, DIG. 26, 205.25, 128/206.18; 604/79, 94.01, 93.01, 95.04
See application file for complete search history.

(56) References Cited

U.S. PATENT DOCUMENTS

| | | | |
|---|---|---|---|
| 2,168,705 A | | 8/1939 | Francisco et al. |
| 2,245,969 A | * | 6/1941 | Francisco et al. ...... 128/207.18 |
| 2,259,817 A | | 10/1941 | Hawkins |
| 2,590,006 A | | 3/1952 | Gordon |
| 2,831,487 A | * | 4/1958 | Tafilaw ................. 604/174 |
| 3,046,989 A | | 7/1962 | Hill |
| 3,338,538 A | * | 8/1967 | Roche .................. 248/75 |
| 3,682,171 A | | 8/1972 | Dali et al. |
| 3,871,373 A | | 3/1975 | Jackson |
| 4,454,880 A | | 6/1984 | Muto et al. |
| 4,660,555 A | | 4/1987 | Payton |
| 4,782,832 A | | 11/1988 | Trimble et al. |
| 4,808,160 A | | 2/1989 | Timmons et al. |
| 4,932,943 A | | 6/1990 | Nowak |
| 5,113,857 A | | 5/1992 | Dickerman et al. |
| 5,172,688 A | | 12/1992 | Dillon |
| 5,335,656 A | | 8/1994 | Bowe et al. |
| 5,477,852 A | * | 12/1995 | Landis et al. .......... 128/207.18 |
| 5,513,634 A | | 5/1996 | Jackson |
| 5,513,635 A | * | 5/1996 | Bedi ................. 128/207.18 |
| 5,535,739 A | | 7/1996 | Rapoport et al. |

(Continued)

FOREIGN PATENT DOCUMENTS

DE        229378        1/1910

*Primary Examiner*—Henry Bennett
*Assistant Examiner*—Amadeus Lopez
(74) *Attorney, Agent, or Firm*—Thomas C. Saitta; Richard S. Vermut

(57) ABSTRACT

An improved nasal cannula and cannula support structure. In a preferred embodiment, an integrated nasal cannula and cannula support device comprise a semi-rigid mono-lumen cannula design comprising a generally L-shaped mono-lumen strut terminating at its distal end with an oxygen supply barrel. In an alternate embodiment of the present invention designed for use with conventional delivery tube pair cannula designs, a nasal cannula support device includes a ridge pole retainer comprising a generally L-shaped strut having a long leg and a short leg. The cannula support is anchored to the wearer's nose and/or forehead such that the cannula delivery tubes and supply barrel are maintained in fixed alignment regardless of the wearer's head motion.

26 Claims, 7 Drawing Sheets

U.S. PATENT DOCUMENTS

| | | |
|---|---|---|
| 5,669,377 A | 9/1997 | Fenn |
| 5,685,292 A * | 11/1997 | Fenn .................... 128/200.24 |
| 5,735,272 A | 4/1998 | Dillon et al. |
| 5,752,511 A | 5/1998 | Simmons et al. |
| 5,803,066 A | 9/1998 | Rapoport et al. |
| 5,817,039 A | 10/1998 | Raunig |
| 5,931,854 A | 8/1999 | Dillon |
| 5,961,537 A | 10/1999 | Gould |
| 5,976,173 A | 11/1999 | Berke |
| 6,093,169 A | 7/2000 | Cardoso |
| 6,328,038 B1 | 12/2001 | Kessler et al. |
| D479,327 S | 9/2003 | Hansen |
| 6,669,712 B1 * | 12/2003 | Cardoso .................... 606/199 |
| 2003/0034030 A1 | 2/2003 | Carlucci et al. |
| 2003/0172936 A1 * | 9/2003 | Wilkie et al. .......... 128/207.18 |

* cited by examiner

NASAL CANNULA

CROSS REFERENCE TO RELATED APPLICATIONS

This application claims the benefit of U.S. Provisional Application Ser. No. 60/409,771 entitled "IMPROVED NASAL OXYGEN CANNULA," and filed on Sep. 10, 2002, and is a continuation-in-part of and claims the benefit of U.S. patent application Ser. No. 09/994,571, filed on Nov. 27, 2001 now U.S. Pat. No. 6,669,712 entitled "NASAL OXYGEN CANNULA WITH SUPPLY TUBE MANAGEMENT," the contents of which are incorporated herein by reference.

BACKGROUND OF THE INVENTION

1. Technical Field

The present invention relates generally to nasal oxygen cannula technology, and in particular, to an apparatus and method for stabilizing and anchoring nasal oxygen cannulas in a secure and comfortable manner.

2. Description of the Related Art

Nasal oxygen cannulas are utilized to deliver oxygen directly to nasal airways in order to infuse oxygen into the inspirational airflow of patients in need of such therapy. Typically, these systems include a relatively large bore plastic supply tube as a conduit for providing gas flow from a pressurized oxygen source to proximal ends of a pair of plastic oxygen delivery tubes having relatively smaller bores. In a typical nasal cannula configuration, the distal ends of the delivery tubes enter into opposite ends of a short, expanded piece of plastic tubing, referred to herein as an oxygen delivery barrel. In the foregoing manner, the oxygen delivery barrel joins the two oxygen delivery tubes in a loop configuration. The barrel is typically cylindrical in shape, formed of a short length of enlarged plastic tubing provided with smaller diameter, stub-like extensions referred to herein as cannula delivery ports. The ports are open at their distal ends and are positioned in circumferential alignment upon the barrel and transverse to the longitudinal axis of the barrel. The cannula delivery ports are positioned so that the distance therebetween approximates an average distance between the nares in which they will be positioned. The terms "cannula," "nasal cannula," and "nasal oxygen cannula" are utilized throughout this specification and within the claims interchangeably, and refer, collectively and individually to an apparatus or device comprised of various tubing and associated retention/anchoring structure for delivery oxygen or other respiratory gases or mixtures of respiratory gases to a patient through the patient's external nasal passages.

An example prior art nasal oxygen cannula design is depicted in FIG. 1. Starting at the distal end, as shown in FIG. 1, the nasal cannula includes a tube coupler 62 designed to mate to an oxygen supply tube fitting (not depicted) on its proximal end. The distal end of tube coupler 62 joins with a single lumen supply tube 64 that branches into a pair of oxygen delivery tubes 68 which in turn terminate at an oxygen supply barrel 63. With the bores of the oxygen supply tube, oxygen delivery tubes, oxygen supply barrel and delivery ports in mutual fluid communication, oxygen is supplied from a pressurized oxygen source to the proximal end of the single lumen supply tube 64 from which it flows into delivery tubes 68 and into the patients nasal passages through a pair of oxygen ports 65 protruding from delivery barrel 63. The source oxygen supply is typically pressurized with the patient's inspirational airflow assisting the oxygen intake.

To ensure adequate and uninterrupted oxygen delivery, nasal cannulas must be securely positioned such that the delivery ports on the oxygen supply barrel are maintained in secure alignment with a patient's nostrils. Conventional catheter/cannulas have largely depended upon the use of the pair of oxygen delivery tubes, such as those depicted in FIG. 1, to stabilize the barrel's position under the nose and thereby maintain the cannula delivery ports within the patient's nostrils. By looping each of two delivery tubes over the top of each ear, a portion of the tube becomes trapped in the sulcus area between the ear and the skin of the head. The traction provided by trapping the tubes within the sulcus, prevents free movement of the delivery tubes and thus provides stabilization of the oxygen delivery barrel under a patient's nose.

The delivery tube ear loop design of the apparatus shown in FIG. 1 achieves limited cannula stabilization that resists displacement of the delivery ports upon movement of the patient's head. However, there are also many disadvantages and limitations related to utilizing this conventional apparatus and method. For example, patients tend to move their heads during sleep, resulting in an associated movement of the pair of oxygen delivery tubes looped behind the ears. Movement of these tubes often causes irritation, abrasion and pain arising from friction at the skin folds comprising the sulcus between the ear and lateral head area. Responsive to such irritation and pain, patients often "shake off" the catheter/cannula resulting in considerable sleep interruption and, more importantly, interruption of the patient's necessary oxygen supply.

The above-described cannula positioning/retention problems are, to some extent, addressed by U.S. Pat. No. 6,093,169 (the '169 patent). To improve retention of the cannula delivery ports within the nostrils, the '169 patent discloses a detachable retainer that is positioned along the ridge pole of the nose. The ridge pole retainer is generally configured as an L-shaped strut having a long "leg" and a short "leg." The long leg of the strut is configured and adapted to conform to and lie upon the ridge pole of the nose from the root of the nose to an area proximate to the tip of the nose. The strut is comprised of a flexible material such as a plastic or fabric covered/padded metal framework that may be secured to the ridge pole of the nose with a suitable adhesive means. The short leg of the strut lies in an angular relationship with the long leg such that it may be positioned under the nose, generally in line with the nasal septum.

The short leg also includes, in certain preferred embodiments, a curved portion that is especially adapted and configured to pass around and securely retain an oxygen delivery barrel. The barrel is thus held and secured in a position and orientation that assures that cannula delivery ports protruding transversely therefrom remain secured within a patient's nostrils.

As described above, the device disclosed by the '169 patent is advantageously comprised of a springy plastic or springy metal backbone demonstrating high elastic memory within operational limits. The contour and elasticity of the device provide a traction force to the nose when the device is secured along the ridge pole of a patient's nose. The traction force of the device, so applied and secured, tends to pull the tip of the wearer's nose both upward and inward. More specifically, as the long arm of the retainer is urged upward towards the root of the nose, the short leg flange portion pulls the tip of the nose upward and inward towards the forehead. The pulling upward and inward of the tip of the nose tends to shorten and increase the diameter of the external nasal airway. As a result, the external nasal bore, widened and shortened, provides decreased airway resistance, allowing greater inspiration and more efficient oxygen delivery to the patient, while simultaneously providing improved stabilization and retention of the oxygen delivery barrel under the patient's nose.

Although the device described by the '169 patent provides increased cannula stabilization, it is still utilized with the above-described ear loops in order to further stabilize the device. Thus, although greater stability is provided by the cannula support device described therein, a patient remains susceptible to irritation, abrasion and resultant "throw off" associated with such loops.

What is needed is a nasal cannula device and method of utilizing same, which provides the increased stabilization and increased airway efficiency demonstrated by the '169 patent, while, at the same time, eliminating the use of ear loops and the irritations and abrasions associated with the use thereof. The present invention addresses such a need.

SUMMARY OF THE INVENTION

An improved nasal cannula and cannula support structure are disclosed herein. In a preferred embodiment, an integrated nasal cannula and cannula support device comprise a semi-rigid mono-lumen cannula design comprising a generally L-shaped mono-lumen strut terminating at its distal end with an oxygen supply barrel. In an alternate embodiment of the present invention designed for use with conventional delivery tube pair cannula designs, a nasal cannula support device includes a ridge pole retainer comprising a generally L-shaped strut having a long leg and a short leg. The cannula support is anchored to the wearer's nose and/or forehead such that the cannula delivery tubes and supply barrel are maintained in fixed alignment regardless of the wearer's head motion.

All objects, features, and advantages of the present invention will become apparent in the following detailed written description.

BRIEF DESCRIPTION OF THE DRAWINGS

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

DETAILED DESCRIPTION OF A PREFERRED EMBODIMENT

The present invention is described in a preferred embodiment in the following description with reference to the figures. While this invention is described in terms of the best mode for achieving this invention's objectives, it will be appreciated by those skilled in the art that variations may be accomplished in view of these teachings without deviating from the spirit or scope of the present invention.

The present invention is directed to a nasal cannula support device that provides improved stabilization of the cannula apparatus and associated tubing while eliminating the need for ear loop retention and stabilization. Each of the embodiments of the present invention provide stabilization of the oxygen barrel within a patient's nostrils while managing or eliminating the need for a pair of side-mounted oxygen delivery tubes feeding the supply barrel. Conventional methods for securing the oxygen delivery tubes result in the tubes rubbing and chafing the sulcus area of skin behind a patient's ears, causing significant patient discomfort and increased potential for intentional or unintentional removal of the apparatus by the patient. The present invention reduces the frequency of cannula loss/displacement, decreases the need for replacement of same by nursing staff, and increases patient comfort.

In a preferred embodiment, an integrated nasal cannula and cannula support device comprise a semi-rigid mono-lumen cannula design comprising a generally L-shaped mono-lumen strut terminating at its distal end with an oxygen supply barrel. In an alternate embodiment of the present invention designed for use with conventional. delivery tube pair cannula designs, a nasal cannula support device includes a ridge pole retainer comprising a generally L-shaped strut having a long leg and a short leg. The cannula support is anchored to the wearer's nose and/or forehead such that the cannula delivery tubes and supply barrel are maintained in fixed alignment regardless of the wearer's head motion.

Figure 2A:
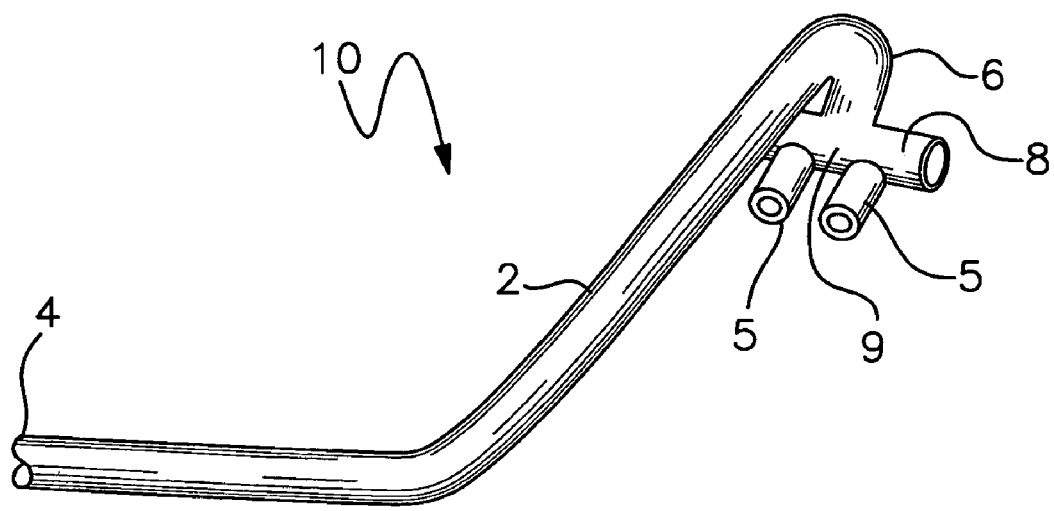
FIGS. 2A–2C illustrate a mono-lumen nasal cannula in accordance with one embodiment of the present invention.
Figure 2B:
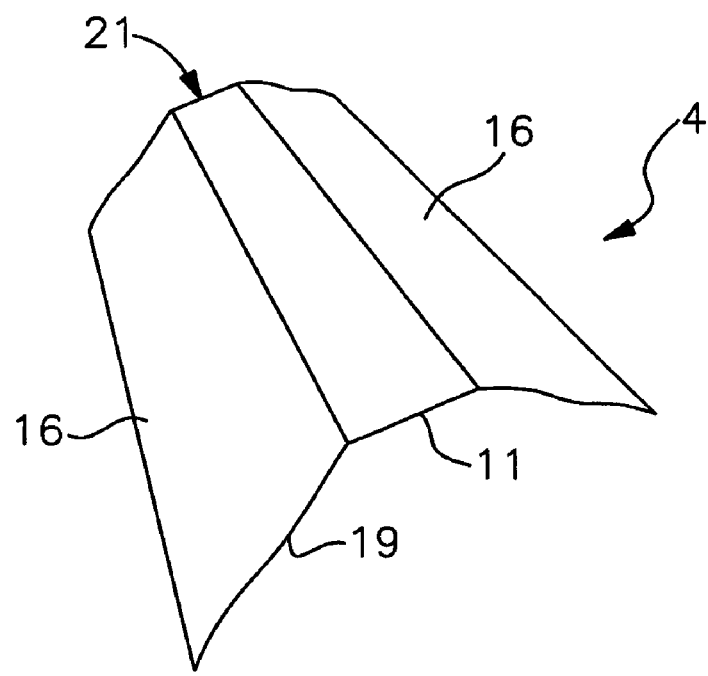
Figure 2C:
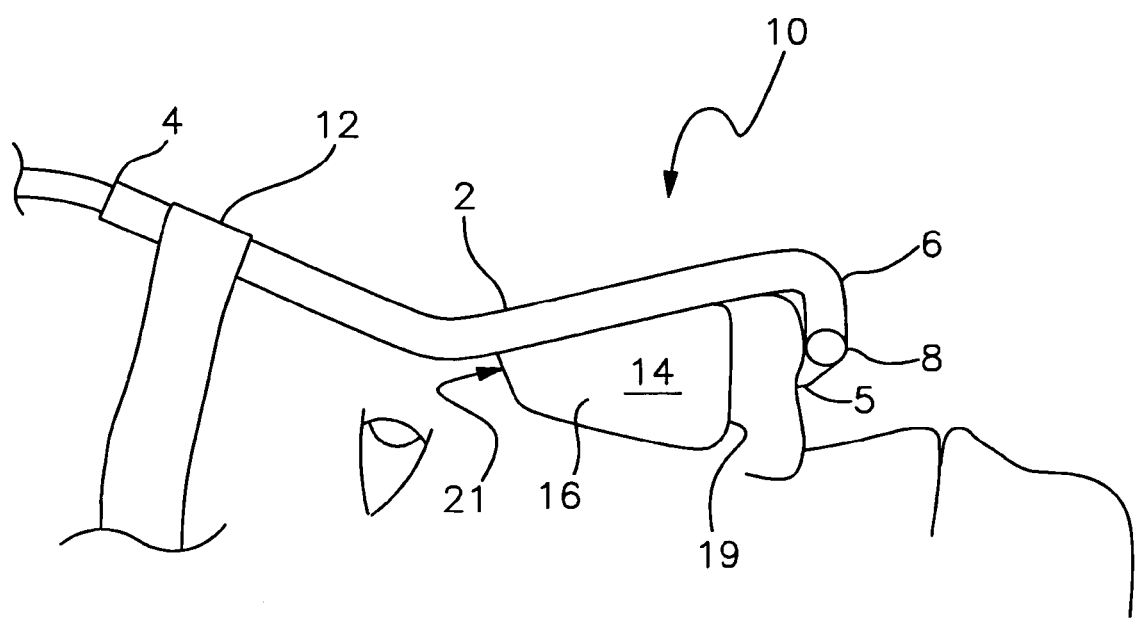

With reference now to the figures, wherein like reference numerals refer to like and corresponding parts throughout, and in particular with reference to FIGS. 2A–2C there is illustrated a mono-lumen nasal cannula 10 in accordance with a preferred embodiment of the present invention. Nasal cannula 10 comprises a mono-lumen tube that is contoured from the forehead down upon the ridge pole of the nose. The material used to construct the tubular portion or nasal cannula 10 is preferably substantially rigid. At its proximal end 4, nasal cannula 10 is coupled to an oxygen supply source (not depicted) such as a flexible feed tube from an oxygen tank or wall fitting. As further depicted in FIGS. 2A and 2C, the mono-lumen body of nasal cannula 10 is formed as a generally L-shaped strut having a short leg or flange 6 angularly connected in a contiguously bending manner to a long leg 2 that rests in generally flush contact with the ridge pole of the patient's nose. In the depicted embodiment, long leg 2 includes an intermediate bend between proximal end 4 and the junction with short leg 6 to accommodate the corresponding contour of a patient's face at the junction between the forehead and nose bridge.

Short leg 6 is contoured to extend over the tip of a patient's nose and terminates at its distal end under the nasal septum with a nosepiece 8. As shown in FIGS. 2A and 2C, nosepiece 8 preferably comprises an enlarged area (compared with the incoming short leg tube diameter) hollow body, and in the depicted embodiment comprise a barrel-shaped body having a septum bearing surface 9 from which intra-nasal ports 5 extend in general alignment with the patient's nares.

Figure 1:
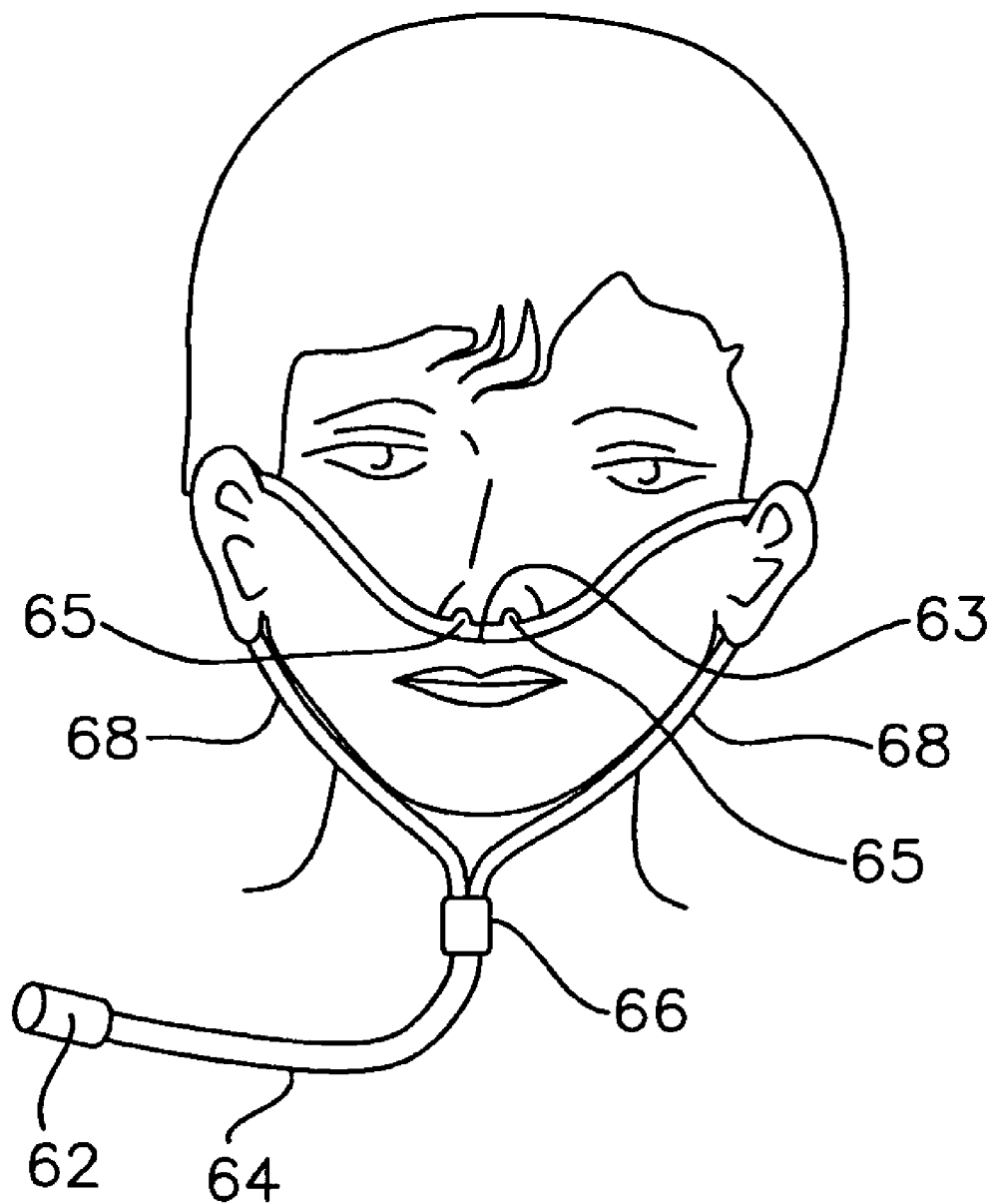
FIG. 1 depicts a conventional dual-lumen nasal cannula apparatus.

The cannula design depicted in FIGS. 2A–2C is a significant departure from conventional designs in which the oxygen supply barrel is fed by two oxygen delivery tubes mounted at each end of the barrel (see FIG. 1). Specifically, the present nosepiece 8 is sealed at its tranverse ends and is fed by short leg 6, comprising a single, centrally disposed lumen tube. As shown in the illustrated embodiment, the single short leg feed lumen 6 is preferably conjoined to oxygen delivery nosepiece 8 at an entry port at its approximate midpoint between intra-nasal cannula delivery ports 5. In joining the mono-lumen tubing into nosepiece 8, the angle between the tubing comprising short leg 6 and cannula delivery ports 5 is selected such that ports 5 are positioned in relative parallel alignment with the nasal passages of a patient and enter the top of the "V" formed by the meeting of the septum with the lateral nasal walls and then travel slightly inward along this sulcus.

Referring to FIG. 2C, a slight traction is applied to nasal cannula 10 from a strap or headband 12 that is utilized to secure the proximal end 4 of nasal cannula 10 against a patient's forehead while cannula delivery ports 5 securely anchored within the nares. This traction force is applied against the septum in an inward direction (i.e. from the tip of the nose toward the forehead), resulting in a shortening of the nasal airway and a slight increase in bore of the nares, facilitating airflow therethrough. Strapping the proximal end 4 of nasal cannula 10 at approximately the mid-forehead level facilitates stabilization of the entire device along the axis of the nose as well as maintaining this portion of the device in relative flush contact against the upper ridge of the nose 15.

In a preferred embodiment, forehead band 12 consists of a double layer of fabric material. A relatively narrow channel or pocket (not depicted), just wide enough to enable passage of the proximal end of the tubular strut member of nasal cannula 10 traverses this band at a right angle. The single-lumen tubular strut passes up the length of the nose onto the forehead and then through the pocket. The pocket may be internally coated with adhesive or an attachment tab or other device may be fitted to the tubing to secure it to the headband at a particular level. Once the entire cannula device has been fitted distally with cannula ports 5 inserted into the nares, forehead band 12 is slid slightly toward the top of the patient's head until the desired traction is provided.

Further stabilization of nasal cannula 10 to the patient's nose is provided by the pre-manufactured inclusion or post-manufacture application of a nasal shield stabilizer 14 having a central portion 11 secured by adhesion or manufacturing processing, such as plastic injection molding, to the long leg member 2 and furthermore having lateral wings 16 that are secured to each side of the patient's nose. As shown in FIG. 2C, nasal shield stabilizer 14 is preferably disposed underneath long leg 2 between the top surface of the ridge pole of the nose and the opposing bottom surface of long leg member 2 of the single lumen strut. Nasal cannula 10 may not need to be reinforced if it is molded together with the underlying nasal shield stabilizer 14. The material composition of nasal shield stabilizer 14 preferably provides a semi-rigid support structure that is molded to long leg member 2 to eliminate or reduce the need to reinforce the single lumen tube structure of nasal cannula 10.

For embodiments in which nasal shield stabilizer 14 is not molded together with the lumen tube, various types of materials providing additional strength and rigidity such as springy malleable brass shim stock, which is preferably covered or padded, may be used with a strip of medical application adhesive tape used to bond the tubing to the stabilizer 14.

In the preferred embodiment shown in FIG. 2B, nasal shield stabilizer 14 narrows from its front edge 19, which is fitted near toward the tip of the nose, to its rear edge 21 fitted near the base of the nose. If, instead of manufacturing nasal shield stabilizer 14 and the mono-lumen strut member comprising long leg 2 and short leg 6 as an integrally plastic injection or extruded molding member, the tube/strut member and nasal shield are manufactured as separate pieces, nasal shield stabilizer 14 preferably includes an adhesive surface layer or strip along its central support strip region 11 at which the stabilizer can be adhesively coupled to the tubular strut member. An adhesive layer may be similarly included on the opposing surface of the tubular strut member to provide adequate adhesion.

The lateral wings 16 are preferably constructed either of plastic (if fabricated as an integral unit with cannula 10) or of a thin springy brass shim stock or other deformable material having elastic memory such that although the entire nasal shield stabilizer is manufactured as an originally flat member, the shield may be rolled or otherwise pressed about an internally situated molding object, such as a tubular mold, resulting in lateral wings 16 drooping with sufficient springiness to lightly grasp the body of the nose between the wings. The disposition of lateral wings 16 on both side of the nose provides lateral stability for nasal cannula 10.

Figure 3A:
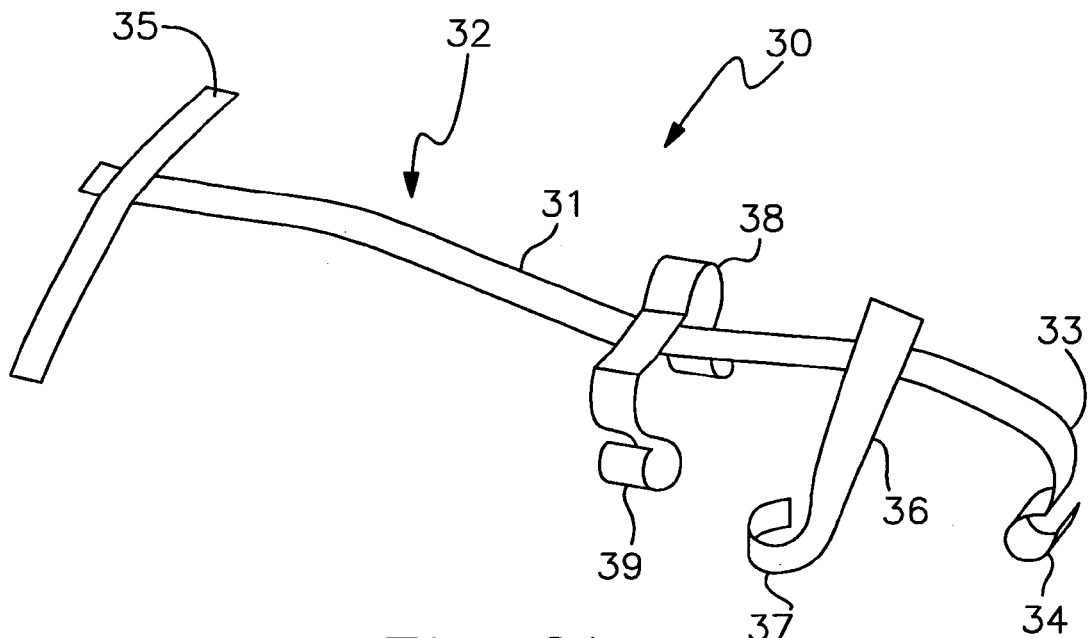
FIGS. 3A and 3B illustrate alternate perspective views of a nasal cannula support apparatus in accordance with an alternate embodiment of the present invention.
Figure 3B:
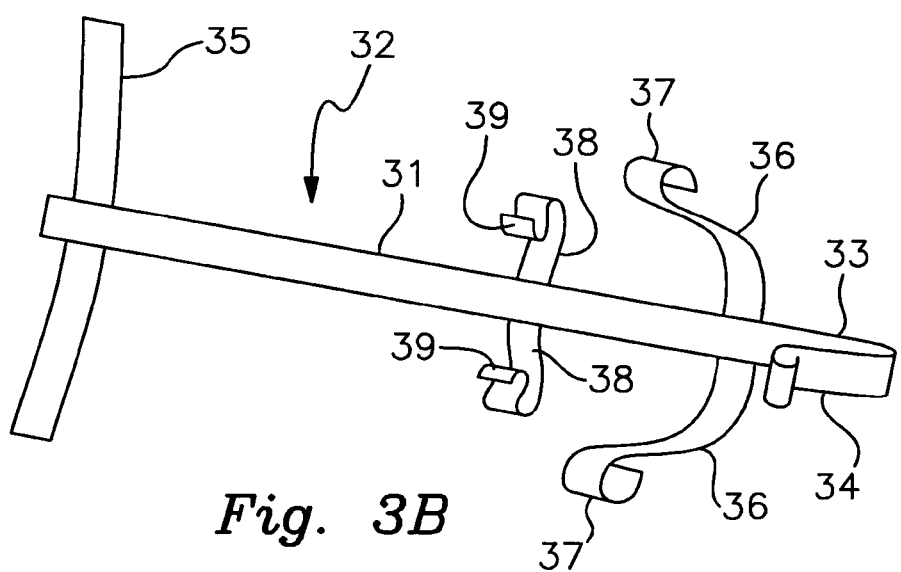

Referring to FIGS. 3–5, there is illustrated a nasal cannula support apparatus for securing a conventional dual oxygen delivery tube cannula design in accordance with an alternate embodiment of the present invention. Specifically, a nasal cannula support apparatus 30 includes a longitudinal support brace 32, which similar to the tubular strut member depicted in FIGS. 2A and 2C, is formed as an L-shaped strut have a long leg 31 upon which various head and nose anchoring features are mounted and a short leg 33 flanging therefrom.

At the distal end of short leg 33, a curved clip portion 34 securely retains an oxygen barrel 44 under the nose and cannula delivery ports 46 within the nostrils. Cannula delivery ports 46 are in fluid communication with the oxygen delivery barrel 44 and a pair of oxygen delivery tubes 43. An oxygen supply source (not depicted) provides pressurized oxygen to an oxygen supply tube (not depicted) which, in turn, communicates at a distal end thereof with proximal ends of the delivery tubes 43.

Figure 5B:
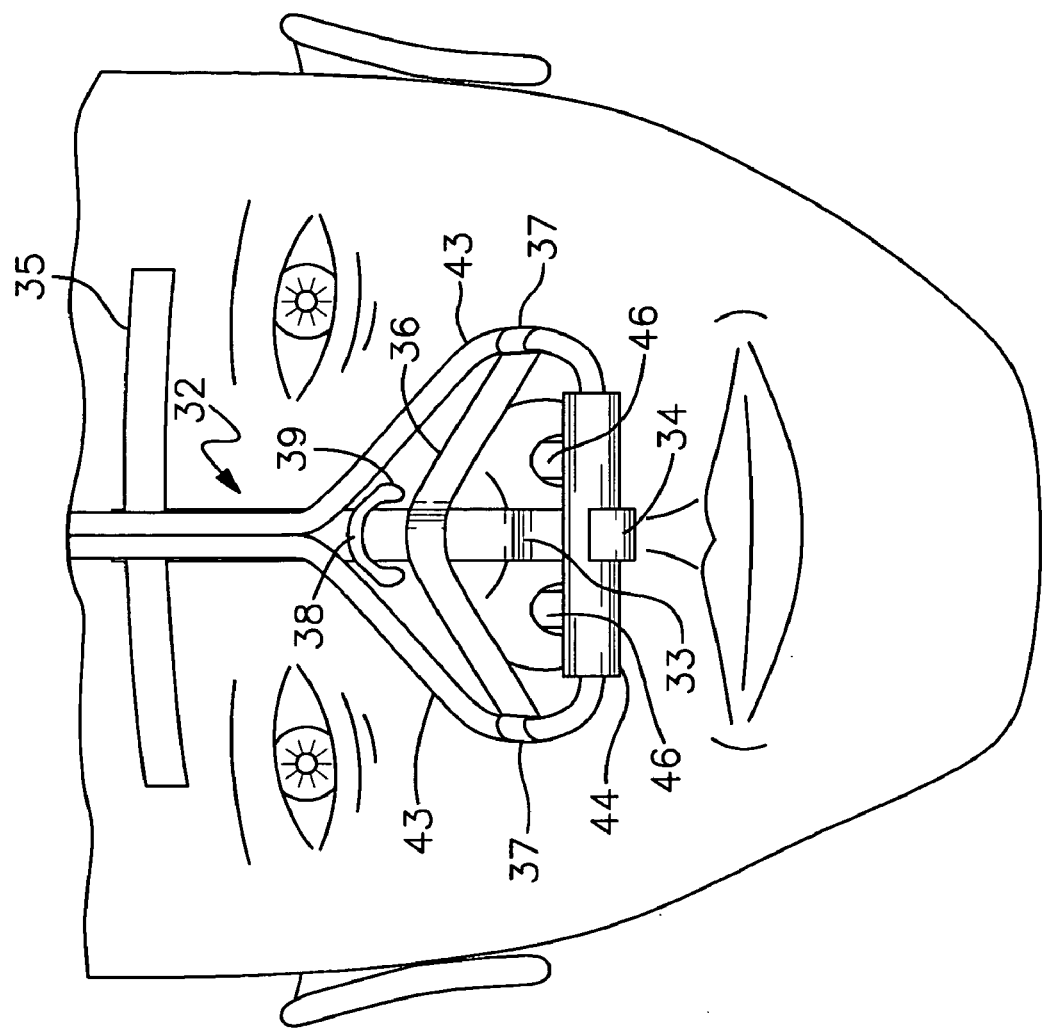
FIGS. 5A and 5B illustrate side and front profile views of a nasal cannula and support apparatus as deployed on a patient in accordance with the embodiment depicted in FIGS. 3A–3B and FIGS. 4A–4B.
Figure 5A:
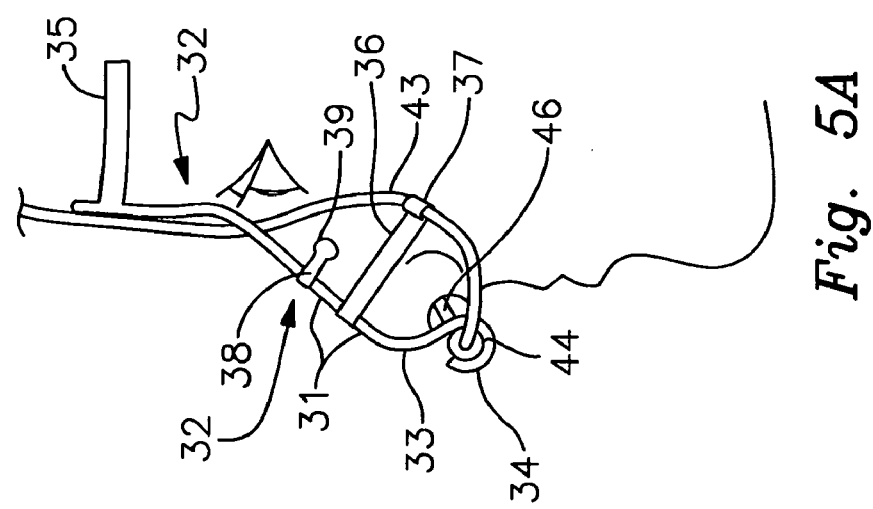

In the depicted embodiment, longitudinal support brace 32 is secured to the nose by means of a cross member 38 having eyeglass-like nasal pads 39 adjustable to rest on each side of the root of the nose. In an alternative embodiment, adhesive tape, adhesive backings, or precision contouring of support brace to conform to the contour of the nose may be used in place of nasal cross member 38 and pads 39 to secure support brace 32 to the nose. As shown in FIGS. 5A–5B, longitudinal support brace 32 preferably extends superiorly beyond the root of the nose to the mid to upper region of the patient's forehead.

In accordance with the depicted embodiment, cannula support apparatus 30 further includes a forehead cross brace 35 for laterally securing longitudinal support brace 32 at a point approximately halfway up the patient's forehead. Forehead cross brace 35 is preferably constructed as a plastic injection molded piece, or in the alternative, may be made of springy brass shim stock, a strip of adhesive tape or an elastic band. If an elastic headband is used in place of the depicted forehead cross brace 35, the object attachment preferably has sufficient elastic pull to yield a slight upward traction on the clip 34, thus maintaining delivery ports 46 securely anchored within the nares. In a preferred embodiment, the lever action imparted by the headband or cross brace 35 on longitudinal support brace 32 is sufficient to achieve a slight shortening and flaring of the nares, resulting in an increased airway and descreased airflow resistance through the nares.

Figure 4A:
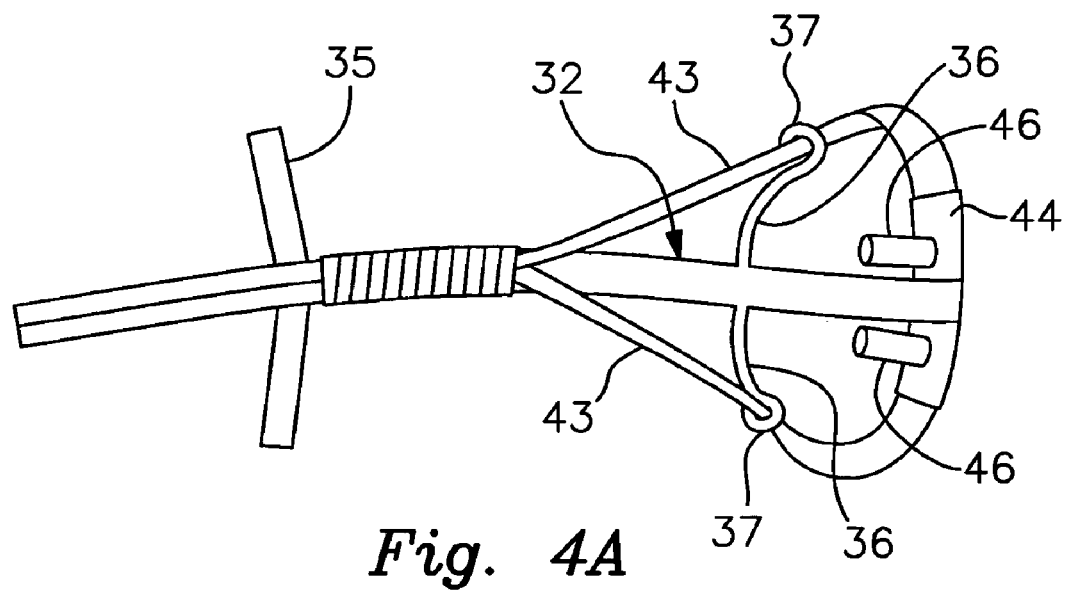
FIGS. 4A and 4B depict alternate perspective views of a combined nasal cannula and support apparatus in accordance with an alternate embodiment of the present invention.
Figure 4B:
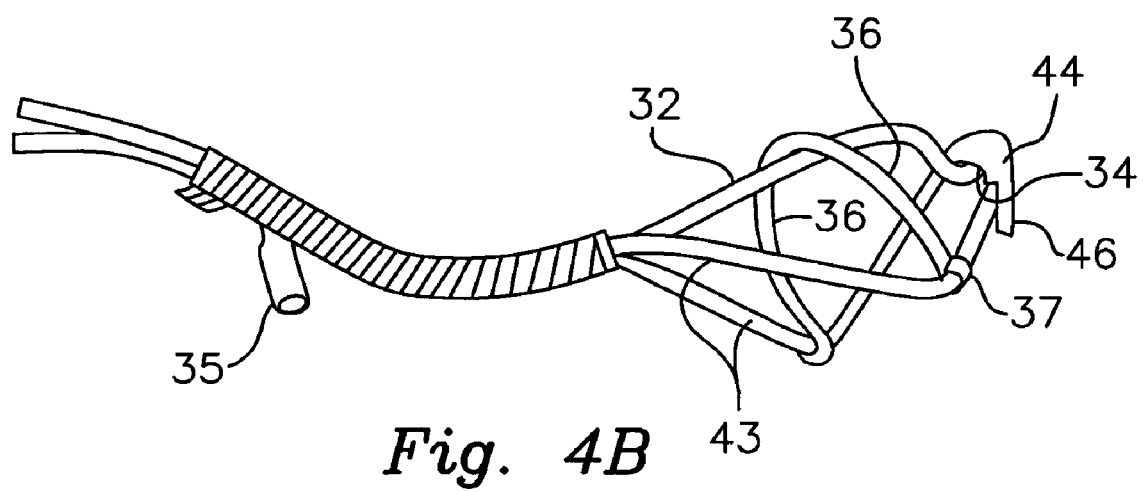

As further depicted in FIGS. 3–5, cannula support apparatus 30 further includes a tubing support cross brace 36 transversely attached to longitudinal support brace 32 below cross brace 38. Tubing support cross brace 36 may be formed as an integral unit with cannula support apparatus 30 using plastic injection molding or may be a separately formed plastic or metallic member soldered or otherwise coupled thereto. As shown in the depicted embodiment, tubing support cross brace 36 includes open-loop clips 37 on each opposing side of longitudinal support brace 32 for retaining the respective oxygen supply tubes 43 on either side of the brace. Referring in particular to FIGS. 4A, 4B, 5A and 5B, the apparatus is deployed as follows. The double branching cannula tubing 43 is coupled to the opposing ends of oxygen delivery barrel 44 which is clipped into loop clip 34 with cannula delivery ports 46 pointing toward the patient's forehead. In this manner, and as depicted in FIG. 5B, ports 46 enter the right and left nostrils with loop clip 34 disposed between and just external to the end of the septum. The oxygen delivery tubes 43 leading away from each end of delivery barrel 44 are led and secured to the opposing sides of the patient's nose by inserting or pushing the tubes 43 into clips 37. From clips 37, the oxygen delivery tubes 43 are led upward and backward in a path centrally and longitudinally aligned with longitudinal support brace 32 and at approximately 1 inch below the boss of the patient's forehead, the tubes are wrapped together upon support brace 32 with tape or other suitable adhesion means.

Figure 6:
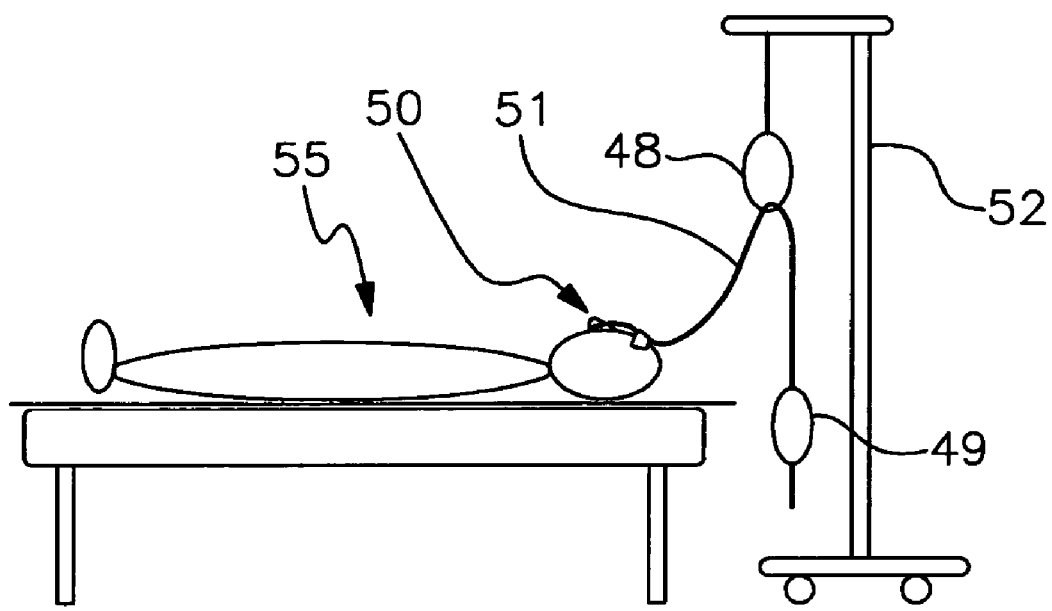
FIG. 6 depicts a nasal cannula support and tube biasing apparatus in accordance with an alternate embodiment of the present invention.

In addition to addressing the problems relating to securing a cannula to a patient's nares and patient discomfort resulting from the traditional behind-the-ears anchoring of nasal cannulae, the present invention further addresses problems relating to the tendency of the oxygen delivery tubes to become snagged in bedclothes or sheets. With reference to FIG. 6, there is depicted an apparatus for managing the cannula oxygen delivery tubing including a means and method by which the nasal cannula can be floated away from the patient to assure the patient's comfort and reduce the chance of snagging and/or removing the cannula. Specifically, FIG. 6 illustrates a patient 55 wearing a cannula support apparatus 50, which may be designed in accordance with the mono-lumen design shown in FIGS. 2A–2C or in accordance with the double branching support shown in FIGS. 3–5. An oxygen supply tube 51 (connected to mono-lumen cannula 10 for the embodiment shown in FIGS. 2A–2C or dual delivery tubes 43 for the embodiment in FIGS. 3–5), is led upward from the patient's forehead and up and through a smooth ring 48 which act as a balance point. Ring 48 may be support by a line from a mobile intra-venous stand 52 or similar support. The length of cannula tubing 51 is maintained in slight tension by a biasing means. In the depicted embodiment, the biasing means comprises a counterweight 49 coupled to the cannula tubing 51 on the other side of ring 48. In the configuration illustrated in FIG. 6, the ring 48 and counterweight 49 provide a sufficient biasing force on cannula tubing 51 to float the tubing above and away from the patient and is a valuable adjunct in maintaining the patient's comfort. In this manner, the present invention reduces or eliminates excess oxygen tubing, thus reducing the susceptibility of the cannula to be unintentionally avulsed. The length of cannula tubing 51 between the balance point on ring 48 (or a suitable alternative balance point such as the flat edge of a headboard) and counterweight 49 is preferably selected to allow for the maximum distance the patient's head will travel as he adjusts himself in bed and of a sufficient length to enable the patient to sit up in bed.

While this invention has been described in terms of several embodiments, it is contemplated that alterations, permutations, and equivalents thereof will become apparent to one of ordinary skill in the art upon reading this specification in view of the drawings supplied herewith. It is therefore intended that the invention and any claims related thereto include all such alterations, permutations, and equivalents that are encompassed by the spirit and scope of this invention.

What is claimed is:

1. A nasal oxygen supply cannula and support apparatus comprising:
   a tube formed as a generally L-shaped strut for conforming to the contour of the nose of a wearer, said L-shaped strut having a proximal end connected to an oxygen supply and a distal end connected to a nosepiece having a one or more intra-nasal oxygen delivery output ports;
   wherein said L-shaped strut includes a long leg member shaped to rest in substantially flush contact with the ridge pole of the wearer's nose;
   and further comprising a nasal shield stabilizer including:
      a central strip portion coupled to said long leg member; and
      lateral wings extending from each side of said central strip portion for gripping the sides of the wearer's nose.

2. The nasal oxygen supply cannula and support apparatus of claim 1, wherein said L-shaped strut and said nosepiece are a single component.

3. The nasal oxygen supply cannula and support apparatus of claim 1, wherein said L-shaped strut and said nosepiece are multiple components.

4. The nasal oxygen supply cannula and support apparatus of claim 1, wherein said L-shaped strut further includes a short leg member proximally coupled in a contiguously bending manner to said long leg member such that said short leg member is shaped to extend over the tip of the wearer's nose, said short leg distally coupled to said nosepiece.

5. The nasal oxygen supply cannula and support apparatus of claim 4, wherein said long leg member, said short leg member and said nosepiece are a single component.

6. The nasal oxygen supply cannula and support apparatus of claim 4, wherein said long leg member, said short leg member and said nosepiece are multiple components.

7. The nasal oxygen supply cannula and support apparatus of claim 4, wherein said long leg member is securable to the ridge pole of the wearer's nose in such a manner as to raise and shorten the tip of the wearer's nose resulting in an increase in diameter and decrease in length of the wearer's external nasal airway.

8. The nasal oxygen supply cannula and support apparatus of claim 7, wherein said L-shaped strut is comprised of a material with sufficient elasticity so as to allow said long leg member to be conformed to the external surface contour of the wearer's nose.

9. The nasal oxygen supply cannula and support apparatus of claim 7 further comprising a means for securing said apparatus to the wearer's nose.

10. The nasal oxygen supply cannula and support apparatus of claim 9 wherein said means of securing said apparatus to the wearer's nose is adhesive tape.

11. The nasal oxygen supply cannula and support apparatus of claim 9 wherein said means of securing said apparatus to the wearer's nose is an adhesive applied to an undersurface of said L-shaped strut.

12. The nasal oxygen supply cannula and support apparatus of claim 7 wherein said L-shaped strut is especially shaped, configured and adapted so as to conform to external surface contour of the wearer's nose.

13. The nasal oxygen supply cannula and support apparatus of claim 12 wherein said L-shaped strut is comprised of a material having sufficient pliability and elastic memory as to allow said conformance to the external surface contour of the wearer's nose to provide a means of securing said apparatus to said wearer.

14. The nasal oxygen supply cannula and support apparatus of claim 12, wherein said L-shaped strut and said nosepiece are a single component.

15. The nasal oxygen supply cannula and support apparatus of claim 12, wherein said L-shaped strut and said nosepiece are multiple components.

16. The nasal oxygen supply cannula and support apparatus of claim 1, wherein said nosepiece comprises a hollow body in fluid communication with said L-shaped strut.

17. The nasal oxygen supply cannula and support apparatus of claim 16, wherein said nosepiece further comprises a septum bearing surface from which said one or more intra-nasal oxygen delivery output ports extend in alignment with one or more of the wearer's nares.

18. The nasal oxygen supply cannula and support apparatus of claim 17, wherein said L-shaped strut and said nosepiece are a single component.

19. The nasal oxygen supply cannula and support apparatus of claim 17, wherein said L-shaped strut and said nosepiece are multiple components.

20. The nasal oxygen supply cannula and support apparatus of claim 1, further comprising a headband for securing said proximal end of said L-shaped strut against the wearer's forehead.

21. The nasal oxygen supply cannula and support apparatus of claim 20, wherein said headband is secured to the wearer's forehead such that an inward traction force is applied to secure said one or more intra-nasal oxygen delivery output ports.

22. The nasal oxygen supply cannula and support apparatus of claim 1, wherein said L-shaped strut, said nosepiece and said nasal shield stabilizer are a single component.

23. The nasal oxygen supply cannula and support apparatus of claim 1, wherein said L-shaped strut, said nosepiece and said nasal shield stabilizer are multiple components.

24. The nasal oxygen supply cannula and support apparatus of claim 1, wherein said L-shaped strut is connected in fluid communication with an oxygen supply tube, said nasal oxygen supply cannula and support apparatus further comprising:
  a tube support means disposed behind the wearer's head, wherein said tube support means provides a balance point for said oxygen supply tube; and
  biasing means for applying backward tension on said oxygen supply tube.

25. The nasal oxygen supply cannula and support apparatus of claim 24, wherein said tube support means comprises a ring.

26. The nasal oxygen supply cannula and support apparatus of claim 24, wherein said biasing means comprises a counterweight coupled to said oxygen supply tube.

* * * * *